United States Patent
Rosenblatt

(10) Patent No.: US 6,365,169 B1
(45) Date of Patent: Apr. 2, 2002

(54) POLYMERIC BROAD SPECTRUM ANTIMICROBIAL COATINGS

(76) Inventor: Solomon Rosenblatt, 127 W. 79$^{th}$ St. Apt. 11C, New York, NY (US) 10024

( * ) Notice: Subject to any disclaimer, the term of this patent is extended or adjusted under 35 U.S.C. 154(b) by 0 days.

(21) Appl. No.: 09/409,834

(22) Filed: Sep. 30, 1999

(51) Int. Cl.$^7$ .............................................. A61N 25/34
(52) U.S. Cl. ........................ 424/404; 424/402; 424/443; 424/400
(58) Field of Search ............................ 525/61; 424/443, 424/444, 445, 446, 402, 404, 400

(56) References Cited

U.S. PATENT DOCUMENTS

| | | | |
|---|---|---|---|
| 1,867,222 A | | 7/1932 | Karns |
| 2,381,621 A | | 8/1945 | Schmelkes et al. |
| 2,668,153 A | * | 2/1954 | Hammon et al. ............. 525/61 |
| 3,328,259 A | | 6/1967 | Anderson ..................... 167/84 |
| 3,501,260 A | * | 3/1970 | Tesoro et al. ................. 525/61 |
| 3,840,482 A | * | 10/1974 | Bolto et al. ................... 525/61 |
| 4,031,209 A | | 6/1977 | Krezanoski ................. 424/150 |
| 4,128,633 A | | 12/1978 | Lorenz et al. ................ 424/80 |
| 4,255,415 A | | 3/1981 | Chrai et al. .................. 424/78 |
| 4,323,557 A | | 4/1982 | Rosso et al. ................. 424/28 |
| 4,340,043 A | | 7/1982 | Seymour ..................... 128/132 |
| 4,396,642 A | | 8/1983 | Bolt et al. ................. 427/54.1 |
| 4,524,064 A | * | 6/1985 | Nambu ....................... 424/445 |
| 4,552,138 A | | 11/1985 | Hofeditz et al. ............ 128/156 |
| 4,675,009 A | | 6/1987 | Hymes et al. ............... 604/304 |
| 4,863,972 A | * | 9/1989 | Itagaki et al. .................. 525/61 |
| 5,071,648 A | | 12/1991 | Rosenblatt ............. 424/780.06 |
| 5,679,371 A | * | 10/1997 | Tanihara et al. ............... 525/61 |
| 5,981,011 A | * | 11/1999 | Overcash et al. .......... 428/40.9 |
| 6,039,972 A | * | 3/2000 | Barlow et al. .............. 424/445 |

FOREIGN PATENT DOCUMENTS

| | | | | |
|---|---|---|---|---|
| CA | 704034 | * | 2/1965 | ................. 525/61 |
| JP | 48-24440 | * | 7/1973 | ................. 525/61 |
| WO | WO/90/04611 | * | 3/1990 | ................. 525/61 |

* cited by examiner

Primary Examiner—Thurman K. Page
Assistant Examiner—Humera N. Sheikh
(74) Attorney, Agent, or Firm—St. Onge, Steward, Johnston & Reens LLC

(57) ABSTRACT

A sustained and controlled release form of iodine is achieved by a complex of polyvinyl alcohol starch and iodine, characterized by the PVA based coating being insoluble in boiling water. The polyvinyl alcohol is in the form of a coating reacted with varying types of non-mineral acid containing catalysts/curing or insolubilizing agents deposited on cellulose sponge or other substrates and subsequently complexed with iodine. These cost effective sponges or wipers are topically applied as a solid state antimicrobial device, which releases controlled amounts of iodine on contact sufficient to kill germ cells, and leaves minimal residue.

8 Claims, No Drawings

POLYMERIC BROAD SPECTRUM ANTIMICROBIAL COATINGS

FIELD OF THE INVENTION

The present invention relates to polymeric coatings which comprise reaction products of polyvinyl alcohol (PVA) which are insoluble in boiling water and subsequently complexed with iodine and/or borates that exhibit antiseptic, broad-spectrum antimicrobial activity in a controlled and sustained manner. More specifically, the present invention relates to a method of rendering a polyvinyl alcohol substrate coating insoluble in boiling water by using non-mineral acid catalysts and specific curing agents.

DESCRIPTION OF THE RELATED ART

Disinfectants can be defined as chemical agents that kill pathogenic organisms. Disinfection is directed against fungi, viruses, bacteria and eukaryotic parasites, such as Giarda. Traditional disinfectants act in dilute solutions by diverse mechanisms, to kill microorganisms, but can leave potentially contaminating residues behind. When applied to animate surfaces, some disinfectants may be undesirable because they also can leave rather high residual concentrations behind on the wound surface, which can adversely affect surrounding healthy tissue. Iodine is an example of a very effective disinfectant which is active in parts per million, but damaging to healthy tissue in larger amounts. In the liquid forms currently commercially available, the amount of iodine administered cannot be controlled. Other typical disinfectants include sodium hypochlorite/Chlorox, aqueous and alcoholic iodine, povidone iodine, aqueous silver nitrate, hydrogen peroxide, phenol, alcohols, benzalkonium chloride, etc.

Solid phase disinfectants are known as "contact" antimicrobials that require that the pathogenic microorganisms contact a biocidal surface, which then release an antimicrobial agent. Some solid phase disinfectants release this toxic dose of disinfectant to microorganisms upon contact, leaving very little extra or residual disinfectant behind in the absence of any microorganisms. These are called demand solid phase contact release disinfectants. Iodine, in certain complexed forms, can be such a disinfectant, and, in addition, even have some capability to differentiate between the proteinaceous matter of bacteria and the proteins present in surrounding healthy tissue. This PVA/iodine starch complex will therefore lose less specificity or effectiveness against the bacteria. Most disinfectants are soon rendered ineffective, since they are reactive toward diluting body fluids and tissue. Well known, demand release type disinfectants include strong base anion exchange resins described in U.S. Pat. No. 5,431,908, and other U.S. Pat. Nos. 3,817,860 and 3,923,665, describing other types of ion exchange resins that bind or complex iodine for use in water treatment disinfection. Insolubilized PVA/iodine complexes, even though not an ion exchange resin also releases small, controlled amounts of iodine (U.S. Pat. No. 5,071,648), which performs as a solid phase antimicrobial on contact, and can also be formed into a useful coating.

U.S. Pat. No. 5,071,648, discloses a post treatment insolubilizing process for forming a free standing film. However, insolubilizing the free standing film requires its post immersion in a solution of formaldehyde and sulphuric acid to cause the acetal cure and insolubility. U.S. Pat. No. 5,071,648 also discloses effective antimicrobial polyvinyl acetal sponge wipes. However, they are generally too costly for most applications because they are based in its entirety on one expensive material (PVA sponge) and also because of this limitation, cannot form the various shapes and combinations necessary to fulfill many industrial and consumer needs.

U.S. Pat. No. 5,071,648 also discloses another free standing film forming process for forming highly insoluble films, which resin solution also contains formaldehyde and sulphuric acid to form insoluble acetals. It further describes a coating of a matrix reinforcement which is sized with pure PVA, without a curing agent, to be subsequently complexed with iodine. However, these sizing coatings are not highly insolubilized, nor do they have to be, as they are proposed for use in non-wiping applications, e.g., to create a single use antiseptic area or environment for application to surgical drapes, gowns and wet dressings, which do not require high coating strength, as would be necessary in a multi-use wiping or scrubbing product.

The prior art in general also teaches coating a PVA foam onto a polyester (Dacron) reinforcing substrate which resin formula also contains mineral acid and formaldehyde curing agents to form acetal cures. These non-iodine complexed PVA foam products are used as car chamois and sport toweling. Polyester is resistant to mineral acid attack, but polyester is limited in the forms available, e.g. no sponges or papers, and the prior art does not describe iodine complexing these polyester reinforced PVA foam sheets.

It is important to note that in order to deposit insolubilized PVA onto a cellulose substrate, previous to iodine complexing, the insolubilizing components of the PVA coating solution must not contain a component that can substantially attack or break down the substrate. Since mineral acid catalysis to form insoluble acetals is the means by which PVA in the prior art is commonly cured, and mineral acids break down cellulose sponges, papers, and cotton cloths, etc., other means by which PVA can be insolubilized are required. In addition, the alternative PVA curing or insolubilizing agents also must not attack cellulose, and must effectively and economically cure the PVA without interfering with the subsequent step of iodine complexing.

The present invention provides a method of making highly insolubilized PVA coatings without the use of mineral acids. Surprisingly, the insolubilizing PVA agents of the present invention not only do not degrade the cellulose substrate but also do not interfere in the iodine complexing reaction, permit a more controllable iodine release with wider applicability at less cost.

SUMMARY OF THE INVENTION

It is the object of this invention to provide a method for preparing less expensive, more widely applicable antimicrobial sponges, cloths and papers.

It is also the object of this invention to form highly insoluble PVA non-mineral acid catalyzed coating (not soluble in boiling water) systems for depositing on, and interstitially onto a variety of readily available, inexpensive, e.g. cellulose derived, or other economical substrates without attacking such substrates.

It is a further object of this invention to complex this coating with iodine and/or borates, to produce controlled iodine release coating materials inexpensively, in the form of conventional cellulose sponges, cloths, papers, non-wovens, etc.

It is a further object of this invention to control the amount of iodine content, and its release, by controlling the amount of insolubilized PVA on the substrate to which it is complexed.

It is also another object of this invention to mix PVA with other iodine compounds and/or iodine complexing materials that are also compatible with PVA and/or iodine.

DETAILED DESCRIPTION OF THE INVENTION

The present invention provides a method for making a substrate normally not capable of being complexed with iodine, said substrate being made capable of iodine complexing, by coating or impregnating the substrate with a solution containing a PVA polymeric mix that can be rendered insoluble by curing in the presence of a non-mineral acid catalysts and optionally a cross-linking agent, and subsequently iodine complexing to act as a solid state antimicrobial device.

The presence of the curing agent (which is defined herewith as the non-mineral catalyst and optionally the cross-linking agent) of the present invention has an insolubilizing effect, yet still permits the formation of post iodine complexes, and most important, has little or no noticeable effect on the mechanical strength of the substrate receiving the coating, and is economical and allows ease of manufacture.

Preferably, the non-mineral acid catalyst is selected from the group consisting of ammonium chloride, ammonium sulfate and magnesium chloride. Also preferably, the cross-linking agent is selected from the group consisting of amine aldehyde, epoxy, polyol amine, metal salt, metal complex, organo metallic, acid salt and organic acid anhydride. Preferable crosslinking agents include: melamine formaldehyde and urea formaldehyde as amine formaldehydes; epoxys as polyamid-epichlorohydrins, trimethylol melamine and dimethylol urea as polyol amines; ammonium dichromate as a metal salt; cupra ammonium hydroxide complex as a metal complex; chrome/fatty acid complex or organic titanate as the organo metallics; and maleic anhydride as the organic acid anhydride.

A substrate such as a cellulose sponge is coated with the PVA/curing agent solution, dried and cured at a temperature of about 125–230° F., and its weight noted as to its PVA content. The cured PVA impregnated substrate is washed, if necessary, and is then complexed with an iodine solution containing excess iodine. The sponge is rinsed out to flush out the excess iodine. The weight of the base sponge is subtracted from the cured PVA impregnated sponge, noting its PVA content. Knowing the amount of iodine that complexes with that PVA resin mix under excess iodine conditions, and knowing the weight of the PVA that remained with the sponge, the amount of iodine can be calculated. Thereby, a product can be attained whose iodine content is known and may be specified for each application and market with a designated content of iodine and predictable antimicrobial activity and longevity for the circumstances for which it is intended. If an adjustment in antimicrobial activity is desired, the concentration of the PVA resin mix impregnate can be varied, but still fully complexed with an excess iodine solution. In practice, preparatory experiments will determine the average weight of a group of base sponges that can be assigned to a batch of sponges die cut to the same dimensions, which eliminates weighing each sponge. Also, a designated concentration of PVA resin mix will be chosen that when impregnated and squeezed out under a set pressure and gap between rollers to achieve a practical reproduceability of resin pickup will eliminate the need for weighing each impregnated sponge and thereby rely more on statistical analysis. After iodine complexing, the sponge is rinsed out of surplus iodine, dried or kept moist, and the cured PVA iodine complex will remain as an insoluble coating, even upon numerous re-wettings and uses. Washed out excess iodine can be recovered by running the wash water through ion exchange resins or by other PVA coated substrates.

The prior art (U.S. Pat. No. 5,071,648) describes an iodine complexed polyvinyl acetal sponge, with desirable antimicrobial properties. The sponge is derived from foamed polyvinyl alcohol, which is acetalized to form an open celled, insoluble matrix, which is totally capable of complexing iodine on or throughout its matrix. Since the bulk material of the sponge, and the iodine complexing component of the sponge are the same, the amount or weight of iodine complexed with the sponge is proportional to the total amount of sponge material present when the iodine content of the complexing solution is not limited. Therefore, the amount of iodine complexed and the size or weight of the PVA sponge are dependent on each other, e.g. the larger the sponge, the more iodine will be complexed. Since iodine is a very effective antimicrobial agent, most often only a very small amount of iodine release (parts per million only) is generally necessary to be effective. Since a certain amount of bulk is required for handling or for other mechanical reasons, this complexed sponge in the prior art may therefore contain a much greater amount of iodine than necessary for its intended antimicrobial use. Also, if a PVA sponge that needs to contain only a small amount of iodine is desired, the bulk of that sponge may be too small to physically function well.

It is a purpose of this invention to make the amount of complexed iodine present independent from the mechanical requirements of the sponge or its substrate, which forms its bulk, and therefore the iodine content is more controllable. Also, since the substrate can now be separated from the iodine complexing component, a much wider choice of substrates can now be chosen to better suit the varying types and purposes of applications, e.g. absorption, abrasiveness, type of woven or non-woven matrix, texture, bulk and cost. For example, the amount of iodine and/or borate etc. required to achieve the antimicrobial properties can be specified based on the number of uses and the environment in which it is being used. This information is then combined with the kind of substrate needed to physically fulfill its function in order to come up with a fully specified product. The range of uses include industrial scrubbing and sanitizing a steel table in a meat packing plant with an abrasive backed cellulose PVA/I complexed cellulose sponge to personal sanitizing or wiping with a paper based towelette. It is evident that different iodine content and physical product specifications to fulfill the various needs for each use are necessary. Limiting by dilution the iodine availability to complex with the PVA sponge in the prior art is difficult, as the acetalized PVA polymer is very active toward iodine, and therefore the sponge is quick to disproportionately complex with more iodine at its initial contacting sites, leaving more diluted iodine solutions behind to complex with the remainder of the sponge. It has been observed that diluted iodine solutions, especially at increasingly lower concentrations, as would occur during attempts at lowering iodine content during dilute complexing of the PVA sponge, can form weaker complexes with less homogeneous distribution of the iodine with poorer reproduceable antimicrobial characteristics, that may overall be less effective than fully saturated complexes. Also, since the chemistry of forming iodine complexes with PVA and its derivatives (iodine can exist in various states up to I3 in the presence of iodide ion)

is not completely understood, these intermediary or partial complexes also cannot yet be fully predicted. It would therefore be very desirable for ease of manufacture, reliability, quality control, and to maximize antimicrobial effectiveness, to use a controllable amount of PVA in the coating as the means to control iodine content, and keeping the complexing iodine concentration in excess to fully complex the set amount of the PVA coating component, and wash out the excess iodine. Therefore, iodine complexing by saturation, e.g. with excess iodine of the PVA is the preferred method as all the PVA complexing sites are then uniformly satisfied. Thereby, this invention allows for more easily controlling the amount of iodine present, by controlling the amount of PVA coating deposited on and throughout the bulking substrate, and fully iodine complexing the PVA present. Accordingly, the present invention provides the following advantages over the prior art:

1. Cost reduction by allowing for the use of various relatively cheaper types of substrates such as cellulose sponges. Another benefit with the use of a cellulose sponge substrate is that this commercially available household sponge already has an acceptable feel in the consumer's hand, and better frictional properties when wiped across a surface, e.g. the polyvinyl acetal sponges in the prior art tend to grab and curl under during use. However, by choosing the right substrate, the sponges of this invention can be designed to wipe more smoothly. Also, most other sponges, including open cell commercial polyurethanes, polyvinyl chloride coated urethanes and polyester foams etc. can also be coated and complexed at a fraction of the cost of PVA sponges, and, additionally, are widely available in many grades and shapes.

2. Improvement of the softness and handling properties of the sponge system when dry. Pure PVA sponges, when dry, are very hard and brittle, and more difficult to hydrate to achieve softness before use. Shipping moist PVA sponges increases both packaging and shipping costs. Also, pure PVA sponges must constantly be kept moist both during use and storage. Coated cellulose sponges can be less stiff when dry, more easily wet out, and therefore can be more easily stored dry.

3. Improvement of the wicking or moistening rate of the sponge when dry. Pure dry PVA sponge takes much time to wet out to attain its soft, useful state, while intrinsically more flexible dry cellulose sponges, cloths and papers wet out faster because they wick better due to their cellulose fiber content which increases their wicking rate.

4. Increasing the number of iodine release rate options available, by mixing various other iodine compounds and other complexing materials with the PVA iodine complex, e.g. with polyvinyl pyrolidone and starches. In the prior art, only acetalized PVA sponges are complexed with iodine, limiting its applications.

5. Improvement in controlling the rate, quantity and longevity of release of iodine by varying the curing agent.

6. Simplification of the manufacture, and reducing the cost of treating pollutants produced during the manufacture of acetalized PVA sponge. Acetalized PVA sponge plant effluents contain toxic mineral acids and formaldehyde. The manufacturing processes of this invention, such as the coating of inert substrates such as cellulose matrixes with PVA coatings cured as outlined herein result in effluents which are comparatively much less toxic.

To achieve antimicrobial activity on only one surface of the sponge, or a portion thereof, the present invention provides that a base sponge surface designated to be activated may be dipped into the PVA resin mix solution. The migration of the PVA resin mix solution into the base sponge, can be controlled or limited by using higher viscosity PVA derived from higher PVA resin concentrations, or use of higher molecular weight resins which give increased solution viscosities, or reduce the time the sponge contacts the solution, all of which limit the depth of penetration of the PVA solution into the base sponge.

Another approach to applying the PVA iodine complex over a specific surface or onto an upper portion only, is by spraying the PVA resin mix solution, either with air type spray guns or airless types which spray high viscosity solutions, over the selected surface to be activated, curing, and then spraying the iodine complexing solution over the previously dried or partially dried insolubilized PVA treated surface overall, or selectively using masks etc. to form localized PVA iodine complexed patterns. The overall surface is PVA coated, but only selected areas of the PVA are thus complexed to form a black pattern.

This spraying method could reduce the rinsing steps for removal of excess iodine because little excess iodine would be sprayed. Since the PVA/iodine complex is black, the complexed PVA will be patterned a vivid black, especially when applied to a contrasting light colored sponge or other base substrates.

Another process that can apply the PVA/iodine complex selectively is by roller coat printing various patterns and concentrations of PVA resin solution onto the base sponge surface. The PVA pattern is dried/cured in a production line, and either overall sprayed, dipped, or like roller coat printed with an iodine solution, flushing out excess iodine and thus forming a patterned PVA/iodine complex as these uncoated areas having neither the PVA or iodine would be devoid of the black coloration.

Other antimicrobial components can be incorporated into the PVA/iodine solutions to accomplish initial greater antimicrobial effectiveness if these antimicrobial adjuncts were more water soluble than the PVA/iodine complex. Povidone iodine is an example of a well known water soluble antimicrobial that would be compatible with the iodine complexing solution to give quicker antimicrobial action. However, this water soluble component would only be useful if an iodine residue were acceptable.

The present invention also provides for mixing the PVA with other iodine complexing materials that are also compatible with PVA and/or iodine. These additives may increase the release rate and immediate concentration of iodine in the infected environment and be especially helpful in occurrences where large bacterial content is present, and quick effectiveness is necessary. Also, additives may be incorporated to reduce the iodine release rate by forming stronger iodine complexes than with PVA, useful where bacteria populations are smaller, and a longer lived antimicrobial environment is desirable. Applying the iodine complexing solution containing the more water soluble polyvinyl pyrolidone is an example of the former application, starch and starch derivatives such as cyclodextrin halide encapsulates mixed with the PVA is an example of the latter modification. The starches preferably would be used only with inanimate contact surfaces, as starches are generally not biocompatible in certain wound sites. Other antiseptic iodine compounds can be admixed with the PVA to counter various bacterial challenges.

Active PVA iodine complexes are characterized by having a deep blue black color (thinner coatings are light brown or blue) but when the iodine content is dissipating, the blue black color slowly fades away and the substrate's color finally becomes the dominant color, e.g. if the substrate were white, the substrate then turns from black fading to blue or light brown to finally pure white or colorless indicating unmistakable activity, and as an indicator for replacement. This clearly evident color change is very convenient, especially for wound dressings, where decision for changing is made only after time consuming removal and examination. If a clear window film in the dressing showing the color of the dressing is present, this would avoid unnecessary changings. Furthermore, if the color was recently dissipated, there is no immediate need to replace the dressing, as the iodine complex causes a clean environment, for some time after, that inhibits bacterial growth. It is also obvious that this intrinsic property of dramatically changing color on iodine dissipation in dressing may also be a very important benefit for the users of wipers made by this invention. The form and composition of the substrate typically may be household type cellulose or urethane type sink sponges, washcloths, cheesecloth pads, gauze woven or non-woven rayons, papers and polyester non-woven materials, etc. These antimicrobial coated sponges, wipes and cloths are then useful as topically applied cleansing and sanitizing devices, e.g. scrubbers for use in industrial food handling and general sanitizing. Household sanitation, personal hygiene, wound healing dressings, clean room wipes, medical devices, antimicrobial coatings, are some other applications, all whose color change indicator of activity and longevity is critical for effectiveness.

A major advantage of PVA/iodine complexes is that they leave little or no detectable residues on their contacted surfaces. Other antimicrobial wipes, e.g. containing quaternary amines, alcohols, chlorinated cleansers, etc. all leave residues behind that may be toxic or create all organic reactions.

From the above discussions, it is evident that the present invention, in contrast to the prior art, allows the iodine content of the sponge to be a separate and independent consideration from the type and size of the sponge substrate, and does not require acetalized PVA foam to accomplish the complexing of the iodine with a sponge matrix. Sponge matrixes of many types are commercially available that would lend themselves as coating substrates for PVA iodine complexes, e.g. cellulose sponges which are composed of reconstituted cellulose mixed with fibers to give them strength and capillarity. These sponges are commonly used in households because they are inexpensive, absorbent, and relatively strong. They would readily absorb the PVA impregnate solution as the chemical properties of cellulose are similar to PVA, and the bonding of PVA to cellulose would be good. In fact, the PVA should improve the wet strength of the cellulose sponge and bind any loose fibers to reduce linting. Also, since cellulose sponges' dry state is more flexible than PVA sponge when dry, the dry flexibility of the PVA coated cellulose sponge combination is better than PVA sponge alone, especially when thinner PVA coatings are applied. In addition, the fiber content of the cellulose sponge should improve the capillarity of the coated combination and improve the wicking rate compared to dry PVA sponge, and thereby reduce wet out times.

Cellulose sponges are available in many colors, thicknesses and pore size, shapes and embossments. Cellulose sink sponges during normal use act as a microbial culturing environment as cellulose is a nutrient for bacteria as well as the ever present particles of food, which results in an infection of the sponge, possible spread of bacteria, odors in the sponge and its degradation. Iodine prevents the proliferation of bacteria and therefore prevents all of the above.

PVA resins and starches are also especially noted for their sizing properties, useful in the paper, adhesive and weaving industries. PVA resins are used to coat many types of fibers, bonding well to their surfaces to aid in their processing, and PVA suppliers make special grades of PVA to fulfill these needs. These specialty grades of PVA can be adapted to coat many types of fibrous and porous matrixes, e.g. polyesters, metal screens, fiberglass, and urethane foam filters, non-woven cloths, and woven cloths, and when cured, give all these base matrixes iodine complexing potential to produce, e.g. antimicrobial versions of water filters, antifungal and antimicrobial substrates in air conditioning systems. (Legionnaire's Disease was due to the lack of proper disinfection of the air conditioning system). In addition, these specialty grades of PVA, some of which are not best suitable for making PVA sponge, may yield unusual complexes with iodine due to their different degrees of insolubility of their iodine complexes. For example, partially hydrolyzed grades of PVA which contain acetate groups have more water solubility at room temperature than fully hydrolyzed grades, and produce complexes with varying iodine complexing properties. Thereby, mixes of different PVA grades could yield special antimicrobial effectiveness at different exposure times.

Open celled polyether polyurethanes and polyester urethane foams can be impregnated with various grades, molecular weights and concentrations of PVA, to be subsequently complexed with iodine to produce all kinds of antimicrobial sponges. Urethanes with 20–50 pores per inch are best suited for coating with PVA. Inexpensive and disposable products made of combinations of diverse matrixes can be developed by laminating, mixing fibers or otherwise bonding different matrixes. For example, combining a layer of cellulose base sponge to be subsequently iodine complexed with a more abrasive polyurethane sponge, or an abrasive containing polyester pad scrubber, the scrubber portion uncomplexed, will produce a multi-duty performing antimicrobial scrubber and polisher biofilm remover, and disinfectant.

PVA resin provides a much improved wet strength to an absorbent paper substrate while still maintaining some of the paper's hydrophilic and absorbent properties. The paper will also have the typical desirable antimicrobial properties when coated lightly with PVA and subsequently iodine complexed. The PVA thereby performs the double function of supplying wet strength to cellulose pulp and papers and the medium for complexing with iodine. A further benefit that PVA provides to fibrous matrixes is that its excellent coating and adhesive characteristic allows it to bond well to fibers, causing the fibers to be more firmly attached to itself in the yarn, thus forming a stronger, smoother sized matrix, reducing linting, and providing a less adhering, still absorbent, surface. Such a matrix, e.g. coffon gauze, felts, pads, or non-wovens, treated with PVA and iodine produces an excellent all in one antimicrobial non-adhering wound dressing. Another product that can be derived from this technology is a consumer single use personal wipe, e.g. a non-woven antimicrobial Wash and Dry type moist paper towelette or napkin in a traditional moisture retaining foil packet. This disposable product can be carried by the consumer to sanitize suspected eating utensils, telephone mouthpieces, push buttons, bathroom knobs and surfaces, surfaces that are expected to be contacted by a child, and other public handles. These specially sized wipes can be used once—larger, multi-use wipe or wipes with different iodine contents may come in a resealable poly pouch. Surgical masks can be improved by having additional antimicrobial properties with the insertion of a tab of PVA iodine complex coated porous paper in the filtering layers. PVA/iodine antimicrobial activity segments can also be put on surgical drapes and gowns to make them more antiseptic by applying complexed labels, printing or otherwise applying the iodine complex to an insolubilized PVA coating. Areas of the drapes which would benefit most by having an antimicrobial environment would be those surrounding the incision site opening, as well as on the cuffs of the disposable surgical gowns. Insolubilized PVA forms more stable complexes with iodine than uncured PVA, as in the prior art. A more stable complex is defined as having the capability of complexing with more iodine, and retaining it over a longer period of time.

The following are examples of highly insoluble antimicrobial coating processes that can form solid state, slow release iodine complexes, and can be deposited in or on cellulose based or any other substrate.

EXAMPLE #1

Polyamide Epoxy Cured PVA Coating 72.00 grams of a medium molecular weight PVA 15% solution and 62.00 grams of low molecular weight PVA 15% solution, both 98% hydrolyzed grades, are mixed with 21 grams POLYCUP 172 12%, 8 grams of water, and 0.5 grams TRITON x 100 wetting agent, and after thorough mixing, the mix is adjusted to a pH between 9 and 10 with ammonium hydroxide. The resin is poured into a coating tray.

Sheets of paper toweling and prewashed thin cotton cloth are dipped and impregnated and placed between rubber rollers to remove any excess resin. The sheets are suspended in a steam box set at 212° F. for 3 hours. The coating's insolubility is tested by immersing a strip (1"×4") in boiling water. After 1 minute immersion, the coating did not dissolve off the substrate nor was it gelatinous. The cured sheets are submerged under an aqueous solution containing 2% iodine dissolved in a 4% potassium iodide solution for 10 minutes with gentle pulsation. The sheets were then flushed from excess iodine under running tap water, until the water ran clear.

The coated sheets are dark blue to black in color and the color is fast to continuous washings and squeezings for an additional 5 minutes. The antimicrobial cloth is useful as a liner for a denture soaking bath that will maintain an antiseptic environment for dentures for weeks, eliminating the need for daily application of expensive antibacterial denture cleanser tablets. The complexed gauze like cotton fabric could be used as a large wound dressing or as a pad on an adhesive bandage plastic strip. Coated and iodine complexed surgical tape cloth, when coated with adhesive would establish an additional antibacterial environment when taping down wound dressings.

EXAMPLE #2

Methylated Melamine Formaldehyde Cured PVA Coating 72 grams of a medium molecular weight PVA 15% solution and 62 grams of a low molecular weight PVA 15% solution, both 98% hydrolyzed grades, are mixed with 26 grams of water, 1.75 grams of PAREZ 707 80% solution, 1.5 grams of ammonium chloride, and 0.5 grams of TRITON X wetting agent.

After thorough mixing, the resin mix is poured into a tray, and a commonly available yellow household cellulose sink sponge is soaked in the resin mix until saturated. The sponge is then squeezed between soft rubber rollers to both evenly distribute the resin throughout the sponge material and remove excess resin.

The resin impregnated sponge is then cured for 5 hours at 180° F., removed from the oven, and rinsed in tap water to remove any unreacted ingredients including residual ammonium chloride catalyst. Excess water is spun out in a centrifuge. While still damp, the sponge is submerged and palpated under an aqueous solution containing 2% iodine in 4% potassium iodide for 10 minutes and squeezed out. The sponge is then washed in tap water to remove excess iodine and iodide. The coated sponge has a shiny blue black color and is fast to continuing washing under running tap water for 5 minutes. Cross sectioning the sponge indicated a uniform coating throughout and interstitially within the cellulose sponge matrix.

This sponge is useful in general household cleaning and is superior to a regular household cellulose sink sponge because it will not harbor bacteria in the sponge interior, and will sanitize the surfaces it contacts. The sponge also has a built-in clearly evident indicator of effectiveness as it gradually turns from black back to its original yellow color as its antimicrobial properties are dissipated. Absorbent paper such as paper toweling is impregnated and processed as in example 2, dried and chopped up into flakes. The flakes are placed into a tea bag with a string. When immersed in microbe contaminated water and gently agitated, it will disinfect the water.

EXAMPLE #3

Boric Acid Additions

The sponge sample in Example #2 was submerged and palpated under and with the same iodine solution, but also containing 5% boric acid based on the water content of the iodine solution. An alternative method for introducing some borate in the system is to substitute all or a portion of the resin used in Example #2 with a pre-borated, commercially available grade of PVA, e.g., Airco grade HA26.

Gauze coated and complexed per Example #1, cut and rolled to form an ear packing is a very effective way to treat general ear infections. In addition to adding the beneficial antimicrobial properties of borates which also form complexes with the PVA, the boric acid also lowers the pH of the ear canal which further inhibits the growth of acid pH sensitive bacteria that often inhabits the ear canal. Because of the smooth PVA coating, this packing will also have less tendency to stick to a wound site in the ear canal. This iodine/borate combination may reduce the need for antibiotics, which is the too often used treatment for ear infections.

EXAMPLE #4

Ammonium Chloride/Formal Cured PVA 70 grams of a medium molecular weight PVA 15% solution and 50 grams of a low molecular weight PVA 15% solution, both 98% hydrolyzed grades, are mixed with 27 grams ammonium chloride, 21 grams of 37% formaldehyde, 20 grams of water, and 0.5 grams of TRITON X wetting agent. After thorough mixing, the resin mix is poured into a coating tray and a commercially available cellulose sponge which is laminated to a fibrous green abrasive pot scrubbing pad is floated on the surface of the resin mix until it sinks, indicating saturation. The impregnated cellulose sponge/pad is squeezed between soft rubber rollers to both evenly distribute the resin throughout the sponge/pad matrix and remove excess resin. The sponge/pad is cured in a steam box at 212° F. for 3 hours, removed from the steam box and squeezed and rinsed in running tap water to remove unreacted ingredients and residual ammonium chloride. Excess water in the sponge is spun out in a centrifuge.

While still damp, the sponge/pad is submerged and palpated under an aqueous solution containing 2% iodine in 4% potassium iodide for 10 minutes, squeezed out, and then washed again in running tap water to remove excess iodine and iodide. The cellulose portion of the coated sponge/pad is a typical blue black color. The abrasive pad side is a greenish dark orange color because the abrasive pad does not absorb nearly the same amount of complexing PVA resin mix as the highly absorbent cellulose sponge material. This sponge/pad is useful in industrial food handling establishments, e.g. meat packing plants where the sanitizing of stainless steel surfaces coated with fatty residues results in tenacious biofilms, which remain even after soap washdowns, and often requires the use of an abrasive pad to physically disrupt or lift the films off the surface before sanitizing the stainless steel.

After the abrasive pad treatment, the sponge/pad may be turned over to the complexed cellulose side and the surfaces are wiped, dramatically reducing the live bacterial count, and most important, leaving little or no measurable residue of iodine on the sanitized surface. Residues are undesirable as they could contaminate foods newly placed on the sanitized surface. However, if enough water is present during the initial use of the abrasive scrub, only the abrasive side need contact the surface, as the complexed cellulose portion will act as a reservoir source of minute amounts of iodine, which are flushed out through the abrasive pad onto the stainless steel surface.

EXAMPLE #5

Insolubilized Starch/PVA Mixes Complexed with Iodine Coatings

Where durability is secondary to cost, e.g. single use or few use products, except for wound management applications, some of the PVA resin can be substituted by starch. Starches have similar properties to PVA and can insolubilize with the same types of curing agents as PVA, and complex iodine, but does not have the coating strength of PVA polymers. Cooked starch is fully compatible with PVA resins forming smooth mixes and homogeneous coatings. Also, starch swelling in hot water during curing causes the PVA coating to become more porous, having more surface area which may increase rate of iodine complexing and capacity and coating flexibility.

54 grams of a medium molecular weight PVA 15% solution and 43 grams of a low molecular weight PVA 15% solution, both fully hydrolyzed grades, are mixed with 6 grams of corn starch swelled in 76 cc of 140° F. water, 1.75 grams of PAREZ 707 80% solution, 1.5 grams of ammonium chloride and 0.59 grams TRITON X 100 wetting agent are added and thoroughly mixed. The coating procedures of example #2 are followed except that paper is coated with the resin mix and complexed subsequently with the iodine. The result is a blue black paper with increased wet strength that is suitable for use as a sanitizing "Wash and Dry" type towelette. Typical personal single use applications could be sanitizing public bathroom contacting surfaces, sanitizing hands after contact with banisters, restaurant tableware, telephone handpieces, gaming machine and other handles, children's feeding areas etc.

EXAMPLE #6

Other Sponge Substrates

Per Example #2, further cost savings can be achieved by substituting urethane sponge for cellulose sponges. For example, polyester urethane foams reticulated to form an open cell structure with 10–50 pores per inch are sufficiently hydrophilic to be coated and impregnated with thicker resin mixes. Many variations of urethane foam are available as substrates to receive good coatings, e.g. quenched or caustic reticulated grades whose surfaces are etched, which improves resin coating capability. Larger open cell foams that are polyvinyl chloride coated which give the foam better chemical stability to the iodine are also candidates for PVA coatings. Since urethane foams are less absorbing toward PVA than cellulose sponges, the resin concentration may be increased in the impregnate to raise the amount of PVA coating deposited on the urethane foam.

EXAMPLE #7

To Determine Iodine Capacity of an Insolubilized PVA Resin

A glass plate was cleaned in warm chromic acid, flushed, dried and weighed. A coating was drawn down on the glass plate made from resin mix in Example #2, and cured in a steam box at 212° F. for 3 hours. The coating is peeled from the glass plate and allowed to dry suspended at 110° F. for 1 hour and weighed. The unsupported coating is then submerged under a 2% iodine, 4% potassium iodide solution for 15 minutes, flushed thoroughly with tap water to remove excess iodine, and dried at 110° F. for 1 hour. The blue/black iodine complexed coating is then weighed. It was found that 7.30 grams of uncomplexed coating gained 0.34 grams when complexed and now weighed 7.64 grams. From this data it can now be calculated that for each gram of Example #2 resin mix deposited on any substrate when iodine complexed, will combine with 0.046 grams of iodine.

Using the resin's iodine combining capacity data, and knowing how much iodine is required for a particular use, one can now deposit that amount of resin on the substrate that will complex with that amount of iodine. Varying the resin mix concentration and amount of resin remaining in the sponge after squeezing through rollers, controls the amount of resin solids deposited on the substrate.

EXAMPLE #8

Organic Titanate

Per example #1, 2 grams of TYZOR TE organic titanate solution was substituted for the POLYCUP 172, and after thorough mixing, the pH was adjusted between 9 and 10. Cellulose sponges treated with the above mix were cured in a 210° F. oven until a thermocouple inserted into the middle interior of the sponges registered a minimum of 180° F. for 30 minutes. Alternatively, the sponges can be cured at 110° F. overnight. The cured sponges are submerged and complexed under an aqueous solution containing 2% iodine dissolved in a 4% potassium iodide solution and treated as per Example #1. The iodine capacity of the titanium cured PVA resin coating was determined per Example #7, and it was found that for each gram of PVA resin mix solids, 0.031 grams of iodine was complexed.

Other examples of methods for increasing the water resistance of PVA coatings are:

1) Urea Formaldehyde

Use of urea formaldehyde resins with varying ratios of amine to formaldehyde to vary cure time.

2. Inorganic Salts

Ammonium dichromate 2–10% based on the resin and the dried coating exposed to UV light.

Other active metallic compounds, such as cupra ammonium hydroxide, chromic nitrate, and other dichromates in a 10% alcoholic solution make an effective dipping bath to post insolubilized PVA coatings.

3. Heat Treatment

Heating PVA coatings with no curing agents present between 230–400° F. will insolubilize the coating, however, some thermal degradation of the PVA and the substrate may also occur.

4. Acid Buffering Salts

Acidic salts, e.g. ammonium chloride, ammonium sulphate, magnesium chloride, when mixed together, or individually with PVA solution, evaporated and cured at 220° F. minimum, will tend to make PVA coatings less soluble.

5. Ether-Maleic Anhydride Copolymers

The polyvinyl derivative is compatible with the PVA resins and is capable of curing PVA.

Although the present invention has been described in relation to a particular embodiment thereof, many other variations and other uses will become apparent to those skilled in the art. It is preferred, therefore, that the present invention be limited not by the specific disclosure herein, but only by the appended claims.

What is claimed is:

1. A method of preparing a substrate coating containing polyvinyl alcohol wherein said coating is insoluble in boiling water, comprising:
   (i) coating said substrate with polyvinyl alcohol, or mixtures of polyvinyl/alcohol and starch wherein said substrate is selected from the group consisting of urethane sponge, cellulose sponge, paper, cloth, non-woven material, polyvinyl chloride coated urethane, polyester foam, washcloth, cheesecloth pad, gauze woven rayon, gauze non-woven rayon, polyester non-woven wound healing material, dressing, polyesters, metal screens, fiberglass, urethane foam filter, mixed fibers, cellulose, fibrous matrixes, yarn, cotton gauze, felts, paper towelettes, napkins, surgical masks, surgical drapes, surgical dressings, abrasive pot scrubbing pads, polyester urethane foam, and combinations thereof;
   (ii) cross-linking said polyvinyl alcohol on the surface of said substrate in the presence of a non-mineral acid catalyst and optionally in the presence of a cross-linking agent; and
   (iii) complexing said coating with an antimicrobial agent selected from the group consisting of iodine and borate-containing compounds and mixtures thereof whereby said coating exhibits antimicrobial activity.

2. The method of claim 1, wherein said coating is capable of releasing free iodine in the presence of water.

3. The method of claim 1, wherein the sponge is a urethane sponge.

4. The method of claim 1, wherein the sponge is a cellulose sponge.

5. The method of claim 1, wherein the substrate is a sheet of paper.

6. The method of claim 1, wherein the substrate is a cloth.

7. An antimicrobial product which comprises a substrate and a substrate coating prepared according to the method of claim 2.

8. A method of controlling infection, said method comprising topical application of a solid state antimicrobial product which includes an antimicrobially effective amount of a controlled-release agent, said agent comprising iodine in complex with a substrate coating prepared according to the method of claim 1, and said controlled release agent being capable, in the presence of water, of releasing free iodine.

* * * * *